United States Patent [19]

Long

[11] Patent Number: 5,138,868
[45] Date of Patent: Aug. 18, 1992

[54] CALIBRATION METHOD FOR AUTOMATED ASSAY INSTRUMENT

[75] Inventor: Ernest W. Long, Concord, Mass.

[73] Assignee: PB Diagnostic Systems, Inc., Westwood, Mass.

[21] Appl. No.: 654,877

[22] Filed: Feb. 13, 1991

[51] Int. Cl.$^5$ .............................................. G01C 25/00
[52] U.S. Cl. ...................................................... 73/1 R
[58] Field of Search ........... 73/1 R, 1 D, 1 H, 864.24, 73/864.25

[56] References Cited

U.S. PATENT DOCUMENTS

| | | | |
|---|---|---|---|
| 4,235,840 | 11/1980 | Mendoza et al. ................ | 73/864.25 |
| 4,478,094 | 10/1984 | Salomaa et al. .................. | 73/863.25 |
| 4,777,818 | 10/1988 | McMurtry ............................ | 73/1 R |
| 4,790,176 | 12/1988 | d'Autry ............................... | 73/1 H |

*Primary Examiner*—Tom Noland
*Assistant Examiner*—Howard Wisnia
*Attorney, Agent, or Firm*—Gaetano D. Maccarone

[57] ABSTRACT

A method of calibrating pipette position in an automated assay instrument employing a conveyor for holding assay cartridges and a transport for transporting a pipette between various locations is accomplished by alignment of a pipette stem with targets located at various locations within the system. Two targets are located on a tray having a plurality of reservoirs for holding liquid, and one target is located on a dummy cartridge carried by the conveyor. An indicator having a spring-loaded tab is used in conjunction with a pipette stem modified by inclusion of a circumferential slot for receiving the spring loaded tab. The stem is inserted into the indicator and locked therein, with limited sliding being provided by movement of the tab within confines of the slot. Alignment marks are provided on both the stem and the indicator to permit visual alignment of the stem relative to a target upon abutment of the indicator with the target. The height of the indicator along with the displacement of the stem from a reference position is inserted into a microprocessor of the assay instrument.

11 Claims, 9 Drawing Sheets

CALIBRATION METHOD FOR AUTOMATED ASSAY INSTRUMENT

BACKGROUND OF THE INVENTION

This invention relates to a pipette head assembly of an automated assay instrument and, more particularly, to a method and device for calibrating a pipette head assembly, wherein the head assembly is adapted for use with disposable pipette tips.

Various types of chemical tests are performed by automated test equipment, an example of testing of considerable interest being the assay of biological substances for human health care. Automated test equipment allows large numbers of test samples to be processed rapidly. Such equipment is employed in health care institutions including hospitals and laboratories. Biological fluids, such as whole blood, plasma, or serum may be tested to find evidence of disease, and to monitor therapeutic drug levels, by way of example. In the automated test instrument samples of test fluids typically are provided in sample cups, and all of the process steps including pipetting of the sample onto an assay test element, incubation and readout of a test-result signal are performed automatically. The test instrument typically includes a series of work stations each of which performs a specific step in the test procedure. The assay element or cartridge is transported from one work station to the next by means of a conveyor, such as a carousel, to enable the test steps to be accomplished sequentially. The conveyor usually carries a plurality of the assay cartridges, each secured to a specific location on the upper surface of the conveyor. In the usual arrangement, the assay cartridges are spaced apart from each other in berths which are located along the periphery of the conveyor to facilitate automatic insertion and extraction.

In many automated instruments, a pipette head assembly is utilized in combination with disposable pipette tips which are used typically only once, and then discarded so as to eliminate a possible source of contamination of fluids, thereby to prevent errors in the assay results. In such systems, the pipette head assembly is required to pick up a disposable pipette tip, aspirate the appropriate fluid into the pipette tip, such as a sample fluid from a sample cup, and to dispense the required volume of fluid to the assay element. The fluid dispensing system in such instruments must meet various requirements which will be understood better from the following description of the typical manner in which a fluid dispensing assembly operates in an automated instrument.

In a typical construction of an automated instrument, the disposable pipette tips and the sample cups are arranged on carriers which are then placed on a carrier or tray supported by a movable table within the instrument. In one type of instrument, the pipette head assembly is transported horizontally (the X direction) and vertically (the Z direction), and the trays which hold the pipette tips and the sample cups are displaced from the front to the back of the instrument (the Y direction). The conveyor can be in the form of a carousel which carries the assay cartridges with rotational movement within an incubator. Initially, the pipette head assembly is driven downwardly to secure a disposable tip by frictional contact of a stem of the pipette head assembly with the interior of the disposable tip. Thereafter, a predetermined amount of fluid is aspirated into the pipette tip, and the tip is driven to a dispense position above an assay element where a predetermined volume of fluid is dispensed. Upon completion of the dispense step, the tip is discarded and a clean disposable tip secured to the stem of the pipette head assembly for the next dispense step.

The operation of the fluid dispense system is directed typically by software embedded in a microprocessor which controls the operation of the instrument. In order for the assays to be conducted properly, it is necessary that the pipette head assembly and, when present, the disposable tip secured thereto, be positioned accurately for aspiration of fluid and for expression of fluid. It is noted that aspiration of a small amount of fluid from a small plastic cup requires accurate positioning of the pipette tip to insure that no air bubbles are aspirated along with the liquid because of the resulting poor volumetric measurement. The sample cup carriers and the pipette tip carriers are usually formed as molded plastic parts, and their dimensions may vary slightly from one to another. Similarly, the assay elements typically have a molded polymeric housing, the dimensions of which may vary slightly from element to element. Also, in order to obtain a uniformly dispensed sample of liquid within the well of a sample cartridge, it is necessary that the pipette tip orifice be at a precisely controlled location above a central portion of the well of the cartridge.

The foregoing requirements of precision and accuracy in the positioning of the pipette can be accomplished only by a proper calibration of the test equipment to account for any minor variations which may be present in the attitude of a sample tray, and any minor deviations from expected position of the various components of the test equipment. Therefore, for automated assay instruments, it is highly desirable to have a technique for calibrating the fluid dispense system to minimize errors in the assay results which would otherwise occur because of dimensional variations in the various component parts and assay elements.

SUMMARY OF THE INVENTION

These and other objects and advantages are provided by a calibration method which, in accordance with the invention, utilizes existing components and drives of an automated assay system in conjunction with a mechanical indicator for determining the precise locations of a pipette holder stem at various points throughout the assay system. In particular, the invention enables accurate positioning of the pipette above various positions on an assay cartridge and also establishes the precise locations of further components, such as sample holding cups disposed in a tray on a movable table to permit accurate aspiration of liquid reagents.

The mechanical indicator has an inner bore to permit insertion of the pipette holder stem of the pipette head assembly into the indicator. Both the stem and the indicator are provided with alignment markings so that, by sliding the indicator along the stem, precise alignment of the indicator with the stem can be attained. In addition, to provide for secure retention of the indicator upon the stem, the stem is provided with the circumferential slot which receives a spring-loaded tab mounted to the indicator. The width of the slot is oversized relative to dimensions of the tab so as to permit translation of the indicator in the axial direction along the stem, thereby to attain alignment of the indicator with the stem. A portion of a sidewall of the indicator is cut away to form a channel which exposes the alignment marks on the shaft so as to make these marks visible. The alignment marks of the indicator are disposed alongside the channel to permit simultaneous viewing of both sets of alignment marks. Removal of the indicator from the stem is accomplished easily by disengaging the tab followed by retraction of the indicator.

The invention is carried out by placing the indicator on the stem, and then positioning the stem with the indicator upon a target. The automated assay system typically includes a stepping-motor drive for moving the conveyor, e.g., rotating a carousel, and two stepping-motor drives within a transport of the pipette head. One of the transport drives advances the pipette head along a path parallel to a radius of the carousel, and the transport drive advances the head in a direction parallel to the axis of rotation of the carousel. Each of the stepping motor drives can be operated one step at a time for incremental displacement of the pipette head and incremental rotation of the carousel to permit accurate alignment of the head and of the carousel. In addition, an electro-optic detector is provided with each of these drives for defining a reference position, namely, a specific angle of orientation of the carousel, a specific location of the head on the path which is parallel to the carousel radius, and a specific position of the head on the path which is parallel to the rotational axis of the carousel. Furthermore, a table which supports the tray of sample wells is movable by a further stepping motor drive in a direction perpendicular to the foregoing two paths of the transport motion.

With reference to the foregoing coordinate directions X, Y, and Z, calibration in the X and the Y directions is accomplished by use of incremental movement of the stepping motor drives providing for the X and the Y displacement during emplacement of the indicator upon a target of a sample tray. Incremental movement is provided until complete alignment is noted visually by a person operating the assay system. Alignment of the angular orientation of the carousel is accomplished similarly by operating the carousel stepping-motor drive in incremental mode while observing the relative positions of the indicator and a target disposed on a cartridge held in a berth of the carousel. For this purpose, a modified sample cartridge is employed.

For calibrating position of the pipette holder stem in the Z direction, use is made of the alignment marks on the stem and on the indicator. The stepping-motor drive of the transport for movement in the Z direction is advanced past the reference-position detector and, thereafter, is advanced further to bring the indicator in contact with a target on the tray, the stem being advanced further in sliding relation to the indicator until alignment is attained between the two sets of alignment marks. A reference height of the indicator is entered into the microprocessor of the assay system. Since the microprocessor continuously counts the steps of the stepping motors in the respective drives, the positions of the pipette head in terms of the X and the Z coordinates are known relative to the reference points of the X and the Z coordinates. Similarly, the positions of the Y coordinate of the table and of the angular coordinate of the carousel are known by the microprocessor. By combining this data with the alignment data entered during the calibration procedure, the correct positions of the pipette head are known by the microprocessor in terms of the X, the Y and the Z coordinates and, similarly, the correct position of the carousel in an angle coordinate is known by the microprocessor.

BRIEF DESCRIPTION OF THE DRAWING

The aforementioned aspects and other features of the invention are explained in the following description, taken in connection with the accompanying drawing wherein.

DETAILED DESCRIPTION

In order to explain the invention in the method of calibrating pipette positions in an automated assay system, it is useful, first, to describe a suitable assay system employing some form of a conveyor, such as a carousel, with a fluid dispensing system for aspirating liquid reagents into disposable pipettes from sample cups or other reagent wells and delivering the liquids to an assay cartridge on the conveyor. Accordingly, the ensuing presentation begins with a description of the overall system, followed by a description of the process of the invention for calibrating the pipette positions at various locations within the system.

Figure 1:
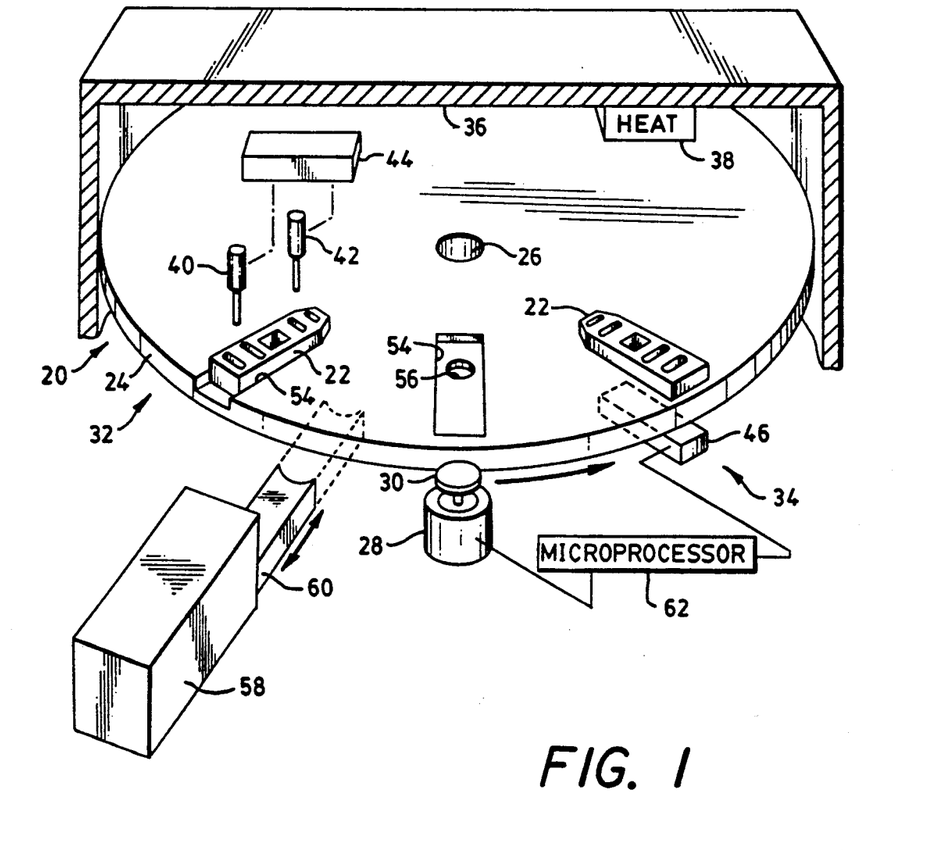
FIG. 1 is a stylized view, partially diagrammatic, of a test system employing assay cartridges, the system employing a carousel for moving the cartridges among various work stations.

In FIG. 1, a test system 20 provides automatically a sequence of chemical process steps to accomplish an assay of a test sample by cartridge 22. A plurality of cartridges 22 are employed within the system 20 to increase the throughput rate, one process step being provided with the contents of one cartridge concurrently with the performance of other process steps with the contents of other of the cartridges. The system 20 includes a turntable or carousel 24 which is rotated about an axle 26 by a motor 28. By way of example, the motor 28 may be mechanically coupled to the carousel 24 by a gear 30 or by a belt drive (not shown). The carousel 24 carries the cartridges 22 from one work station to another work station, two such work stations 32 and 34 being shown, by way of example, in FIG. 1. The carousel 24 rotates within an incubator 36. The incubator 36 has a heating system including a plurality of heaters represented diagrammatically by a heater 38 for maintaining a desired temperature at the various work stations. The maintenance of the desired temperature allows for a process step of incubation, this step being employed in an assay of analytes.

The work station 32 may employ one or more pipettes, two such pipettes 40 and 42 being shown by way of example, for delivering liquid to, and transferring liquid among, various chambers of, a cartridge 22, as will be described hereinafter. The pipettes 40 and 42 are positioned and operated by a pipette mechanism 44 mechanically connected to the pipettes 40 and 42, as indicated by dashed lines. During the assay procedure, as a result of the reaction(s) and interaction(s) between the sample fluid and the test reagent(s) which take place, a detectable change is effected corresponding to the presence of an analyte or component of interest in the sample fluid. The detectable change may be a color change which may be read spectrophotometrically such as with a densitometer or, in an assay method based on fluorescent-labeled biologically active species or one which involves the generation of a fluorescent species as a result of a reaction between test reagents, a fluorescent output signal can be generated and read spectrofluorometrically. Such detectable changes may be read from above or below the assay module or cartridge 22. At work station 34, there is shown, by way of example, a fluorometer 46 for irradiating the reaction zone within the cartridge 22 and for measuring the fluorescence emitted from the fluorescent species present therein.

The carousel 24 may be arranged so as to accommodate varying numbers of cartridges 22. Each position, or berth 54, for holding a cartridge 22 is provided in this embodiment with a small aperture 56 to allow the radiating illumination to reach the reaction zone in the cartridge 22, and to permit the fluorescent emissions to be collected and measured. Also shown is an injector 58 for inserting a cartridge 22 in an empty berth 54, the injector 58 having an arm 60 for gripping a cartridge 22 during the insertion operation. The injector 58 also serves to extract a cartridge from a berth 54 by use of the arm 60 upon completion of a test procedure. Operation of the motor 28, the pipette mechanism 44, the fluorometer 46 and the injector 58 are synchronized by means of timing signals provided by a microprocessor 62.

Figure 2:
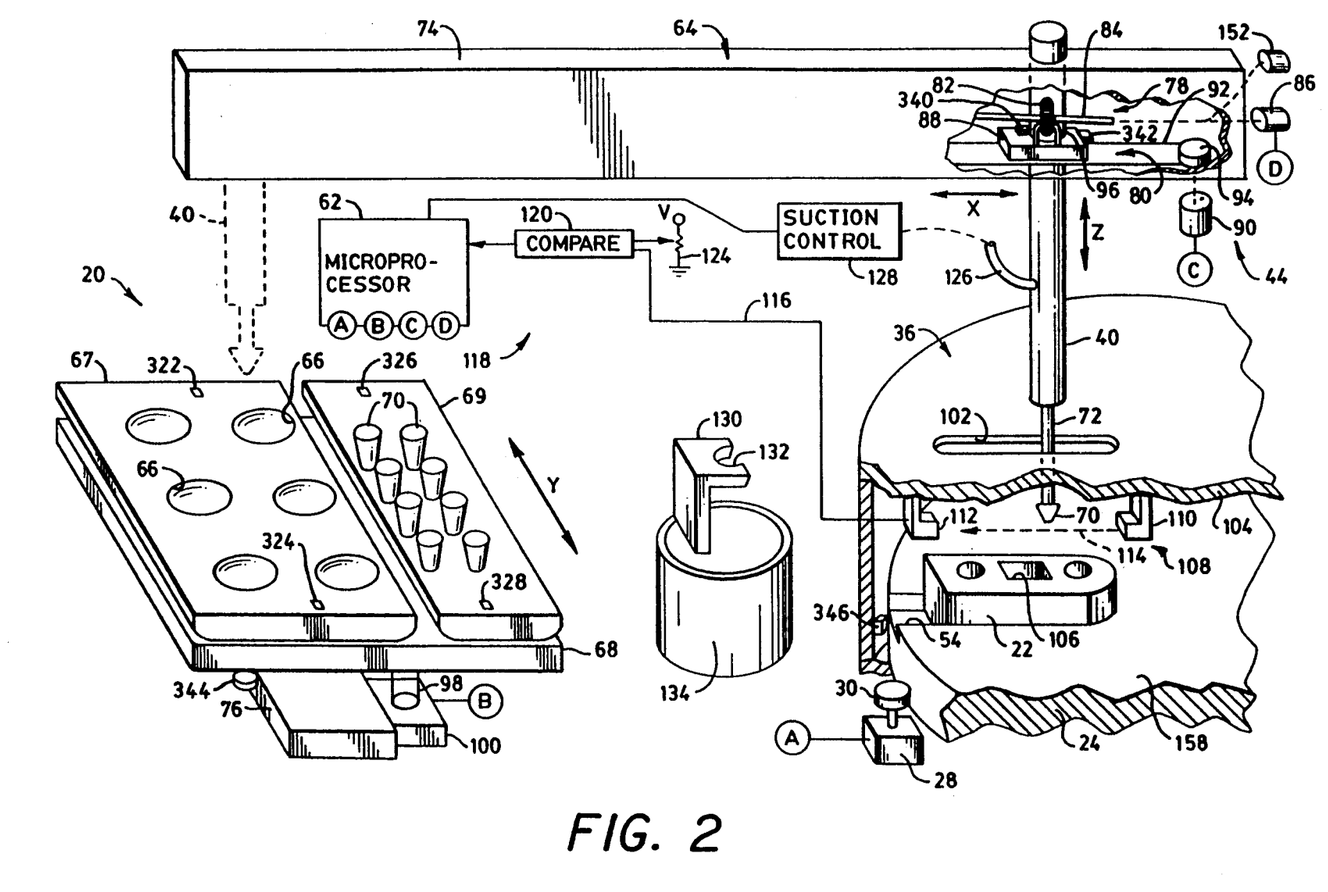
FIG. 2 is a stylized view, partially diagrammatic of a pipette transport for moving the pipette between a supply of tips, sample fluid reservoirs, and compartments of an assay cartridge, the figure showing also an optical detection system for sensing the location of a tip of the pipette.

FIG. 2 provides detail in the construction of the pipette mechanism 44 of FIG. 1. To facilitate description of the invention, the pipette mechanism 44 will be described hereinafter as having a pipette transport 64 operative with only one of the pipettes, namely, the pipette 40. The transport 64 provides for relative movement, in three dimensions, between the pipette 40 and a set of sample cups or reservoirs 66 located at a distance from the cartridge 22, the cups or reservoirs 66 serving to hold the fluid samples which are to be tested by the system 20. The reservoirs 66 are located on a tray 67 carried by a movable table 68 which also carries a tray 69 holding a set of tips 70 which are to be affixed to a stem 72 of the pipette 40. With reference to an X-Y-Z coordinate axes system, the pipette 40 is translatable in the X direction along a box beam 74 of the transport 64, and the table 68 is translatable in the Y direction by riding along a rail 76 of the transport 64. A vertical drive 78 is located within the beam 74 and serves to raise and to lower the pipette 40 in the Z direction. The X coordinate intercepts an axis of rotation of the carousel 24, and is therefore parallel to a radius of the carousel 24, and the Z coordinate is parallel to the axis of rotation of the carousel 24.

A horizontal drive 80 located within the box beam 74 drives the pipette in the X direction. The vertical drive 78 and the horizontal drive 80 are of conventional design, and are indicated in simplified fashion in FIG. 2. In simplified fashion, the vertical drive 78 may be described as comprising a wheel 82 slidably mounted to a spline shaft 84 which, alternatively, may have a square cross section. The shaft 84 is rotated by a motor 86. The horizontal drive 80 includes a base 88 which slides in the X direction along the beam 74 in response to rotation of a motor 90. The motor 90 drives a belt 92 through a pulley 94, the belt 92 being connected to the base 88 for translating the base 88 upon rotation of the pulley 94 by the motor 90. A fixture 96 upstanding from the base 88 slides the wheel 82 along the shaft 84 upon movement of the base 88 so that the wheel 82 strays in fixed position relative to the base 88. The pipette 40 passes through the base 88 so as to be translated in the X direction by the base 88. The wheel 82 is mechanically connected to the pipette 40, as by gear teeth on the wheel 82, or by means of a belt drive (not shown). The mechanical connection of the wheel 82 to the pipette 40 provides for a translation of the pipette 40 in the Z direction upon rotation of the wheel 82 by the motor 86. A belt drive 98 may be employed, similarly, for driving the table 68 in the Y direction in response to rotation of a motor 100 affixed to the rail 76.

As noted above in the description of the system of FIG. 1, the motor 28 is under control of the microprocessor 62. Similarly, the motors 100, 90, and 86 are also under control of the microprocessor 62. Connections of the motors 28, 100, 90, and 86 are indicated in FIG. 2 by terminals A, B, C, and D, respectively. Thereby, movement of the pipette 40 can be synchronized with a positioning of the cartridge 22 by the carousel 24 to a location directly beneath the beam 74. In order to provide access to the cartridge 22 by the pipette 44, a slot 102 is provided in a top wall 104 of the incubator 36. The slot 102 extends parallel to a radius of the carousel 24, and is parallel to the beam 74. The location of the slot 102 relative to the beam 74 permits the stem 72 of the pipette 40 to be lowered through the slot 102 selectively above a desired well or compartment of a plurality of compartments 106 of the cartridge 22. The length of the slot 102 is commensurate with the length of the cartridge 22 to permit displacement of the stem 72 in the X direction for alignment with a selected one of the compartments 106. The slot 102 is relatively narrow, and has a width large enough to clear the stem 72 and the tip 70 mounted on the distal end of the stem 72. With respect to the overall dimension of the incubator 36, the area occupied by the slot 102 is sufficiently small to preclude any significant amount of air flow between the interior and the exterior of the incubator 36. Thereby, the slot 102 has no more than a negligible effect in the control of the incubator temperature, which temperature is controlled by the heater 38 (FIG. 1).

In an embodiment of an automated assay instrument, an optical detection system 108 is provided to signal the microprocessor 62 when the tip 70 of the pipette 40 has advanced in the downward direction to a predetermined distance from the selected compartment 106. The detection system 108 comprises a source 110 of light which, by way of example, may be a semiconductor diode which emits infrared radiation. The detection system 108 also comprises a light detector 112, the light being indicated by a light beam 114. The detector 112, which may comprise a semiconductor photodiode, emits an electric current along line 116 in response to light of the beam 114 incident upon the detector 112.

The detection system 108 includes electrical comparison circuitry 118 for measuring the magnitude of the current on line 116. By way of example in the construction of the circuitry 118, the circuitry 118 comprises a comparator 120 and a resistive voltage divider 124 providing a reference voltage to the comparator 120. The divider 124 comprises a potentiometer for allowing manual adjustment of the reference voltage for initial alignment of the detection system 108. The divider 124 provides for selection of a comparator reference voltage in accordance with the degree of optical transparency of the tip 70.

In the operation of the detection system 108, the full strength of the light beam 114 is incident upon the detector 112 in the absence of the pipette 40. By way of example, the pipette 40 may be at the location of one of the reservoirs 66, as indicated in phantom view of the pipette. During maximum intensity of the received optical signal at the detector 112, a maximum current and voltage appear on line 116. During descent of the pipette 40, the tip 70 interrupts the light beam 114. The line 116 is connected to an input terminal of the comparator 120 which outputs a logic-1 signal to the microprocessor 62 under conditions of maximum illumination of the detector 112, as occurs prior to interruption of the light beam 114 by the pipette 40. Interruption of the light beam 114 greatly reduces the intensity of light received at the detector 112 so that the comparator 120 outputs a logic-0 signal to the microprocessor 62. The extent of the interruption of the light depends on the degree of the transparency of the tip 70. The tip 70 is fabricated typically of a translucent polymeric material.

Liquid reagent is drawn into the pipette tip 70 by vacuum and expelled from the tip 70 by pressure delivered to the pipette 40 by a suction tube 126 under control of a suction control unit 128. The tube 126 is flexible and of sufficient length to connect the suction control unit 128 with the pipette 40 at all locations of the pipette 40. The control unit 128 is connected to the microprocessor 62 which commands the control unit 128 to apply vacuum for inducting liquid, and for releasing vacuum and applying positive pressure, if necessary, to expel the liquid reagent. Induction of liquid sample is done from a selected one of the reservoirs 66. Expelling of the liquid sample is accomplished only when the tip 70 is in the position for dispensing the liquid to the selected one of the compartments 106 in the designated cartridge 22. It is noted also that induction of liquid reagent can be accomplished at one of the compartments 106 of the cartridge 22 to be dispensed in another of the compartments 106. In this respect, a reservoir for storage of liquid reagent can be located directly within the cartridge 22. The location of the various reservoirs 66 of the table 68 is stored in a memory of the microprocessor 62. This enables the microprocessor 62 to move the table 68 to a specific address in the Y direction, and to move the pipette 40 to a specific address in the X direction, the X and the Y components of the address fully identifying the requisite one of the reservoirs 66. In similar fashion, the microprocessor 62 stores locations of the available tips 70 held by the table 68 so that successive ones of the tips 70 can be selected for affixation to the stem 72.

The transport 64 is operative in the process of affixing a tip 70 to the stem 72 of a pipette 40, and in the detachment of the tip 70 from the stem 72. The procedure begins by a lifting of the pipette 40 so that the tip 70 clears the slot 102. The pipette 40 is then free to move along the beam 74 to an extractor 130. The extractor 130 has a semicircular channel 132 cut out in the edge of a horizontal portion of the extractor 130, the channel 132 having a diameter large enough to permit clearance of the stem 72 by the channel 132, but small enough to permit engagement of the channel 132 with the tip 70. Under commands of the microprocessor 62, the pipette is brought towards the extractor 130 with the tip 70 being below the channel 132. The stem 72 enters the channel 132 after which the pipette 40 is raised to engage the tip 70 with the extractor 130. The tip 70 remains stationary as the stem 72 lifts out of the tip 70. Thereupon, the tip 70 falls into a bin 134 for collection of used tips 70. It is advisable to employ the extractor 130 at the beginning of operation of the test system 20 to ensure that the stem 72 is free for reception of a new tip 70.

After ensuring that the stem 72 is free for reception of a tip 70, the pipette 40 is brought, by displacement in the X direction, to a location above the table 68, whereupon the table 68 is translated in the Y direction to bring the stem 72 above and in registration with a selected tip 70 held by the table 68. The pipette 40 then advances downward to make frictional contact with the interior surface of the tip 70. Thereupon, the pipette is raised, and the tip is retained on the distal end of the stem 72 by friction forces.

Figures 3, 4:
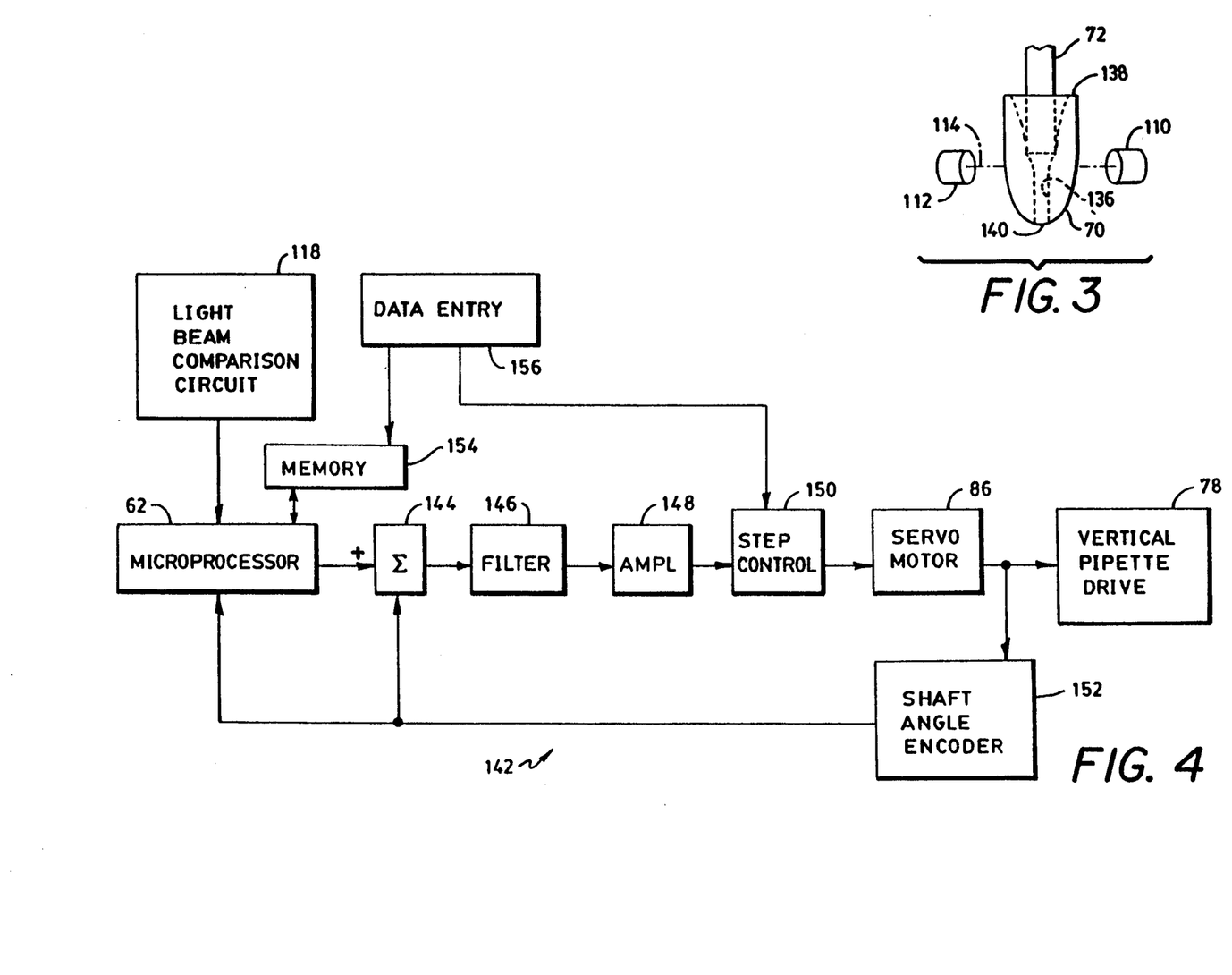
FIG. 3 is an enlarged fragmentary view of a tip of the pipette within a light beam of the optical detection system.
FIG. 4 is a block diagram showing a servo control loop of the pipette transport operative with a microprocessor for positioning the pipette within the vertical direction.

With reference also to FIG. 3, the distal end of the stem 72 is shown making frictional contact with the surface of a channel 136 of the tip 70. The channel 136 extends along a central longitudinal axis of the tip 70 from one end of the tip to the opposite end of the tip. The channel 136 has a circular cross-sectional shape of varying diameter, the diameter being larger at the top end 138 than at the bottom end 140. As the stem 72 advances downwardly into the channel 136, constriction of the channel 136 produces frictional forces which tighten the tip 70 upon the stem 72. These frictional forces are sufficient to ensure a secure attachment of the tip 70 to the stem 72 during transfer of liquid reagent during test procedures of the system 20. However, the frictional forces are sufficiently small to permit the extractor 130 to slide the tip 70 off of the stem 72 upon completion of a transfer of liquid reagent.

With respect to the operation of the system 20, it is noted that the manner of affixing the stem 72 to the tip 70 provides substantial uniformity in the locations of successive tips 70 upon the stem 72. However, in view of the flexibility of the polymeric material of the tip 70 brought about by contact with the relatively rigid tube of the stem 72, and in view of some variation in frictional forces among the tips 70, it has been found that there is slight variation among the locations of the bottom ends 140 of the tips 70 relative to the distal end of the stem 72. This variation is sufficient to serve as a source of inaccuracy to the dispensing of liquid in the compartments 106 of the cartridge 22. The system automatically corrects for these variations in tip location by sensing the location of the bottom end 140 of the tip 70 by means of the light beam 114. The procedure for correcting for the variations in tip location is explained further with reference to the diagram of FIG. 4 and the flow charts of FIGS. 5–6.

FIG. 4 shows a feedback circuit 142 for interconnecting the microprocessor 62 with the motor 86 for operation of the vertical pipette drive 78 disclosed in FIG. 2. As shown in FIG. 4, the circuit 142 includes a summer 144, a filter 146, an amplifier 148, a stepping motor controller 150, a shaft angle encoder 152 (also shown in FIG. 2), a memory 154 of the microprocessor 62, and an entry device 156, such as a keyboard, for entering data into the memory 154. In a preferred embodiment, all of the motors 28, 100, 90 and 86 are constructed as stepping motors.

In operation, for lowering the pipette 40 towards the cartridge 22 (FIG. 2), the microprocessor 62 successively enters new locations on the path of travel of the pipette 40 in the Z direction. Location signals of the microprocessor 62 are applied to one input terminal of the summer 144. The present location of the tip 70, as estimated by the encoder 152 is applied to a second input terminal of the summer 144 to be subtracted from the value input at the first terminal of the summer 144. It is noted that the encoder 152 provides an accurate value of the location of the pipette stem 72, but not of the tip 70, because the position of the tip 70 relative to the stem 72 varies from tip to tip because of the frictional fit explained above. Therefore, a value of shaft angle outputted by the encoder 152 can be taken only as an estimate of the true position of the tip 70.

In accordance with a feature of the invention, it is noted that the invention provides for a calibration of the position of the stem 72, as will be described hereinafter, relative to the tip tray 69. The calibration significantly reduces the foregoing variations in tip position because the stem 72 can be lowered into the pipette tip 70 to a precisely determined location relative to the bottom end 140 of the tip 70.

The signals outputted by the encoder 152 and by the microprocessor 62 are formatted digitally. The summer 144 forms the difference of these two signals and applies the difference as the loop error signal to be filtered by the filter 146. In accordance with the usual practice in the construction of the feedback loops, the filter 146 may be a low-pass filter, and may include a lead-lag filter component. The filter 146 provides stability to the feedback loop. An output signal of the filter 146 is amplified by the amplifier 150, and is applied via the controller 150 to the stepping motor 86. The loop gain and bandwidth, as established by the amplifier 150 and the filter 146, in conjunction with the motor 86 determine the dynamic response of the loop in a manner well known in the design of servomechanisms. The motor 86 rotates towards the rotational position commanded by the microprocessor 62. As the motor 86 rotates, the vertical drive 78 lowers the pipette 40. By way of alternative embodiment in the construction of the feedback circuit of FIG. 4, it is noted that the functions of the summer 144 and the filter 146 can be accomplished directly within the microprocessor 62 by suitable programming of the microprocessor 62. In such a case, the microprocessor 62 outputs the error signal directly to the amplifier 148 for driving the motor 86.

With respect to the circuit shown in FIG. 4, the microprocessor 62 continues to input further values of position along the path traveled by the pipette 40 until the light-beam comparison circuit 118 signals the microprocessor 62 of a break in the light beam. The location of the tip 70 is now known accurately by virtue of contact of the tip 70 with the light beam 114. The pipette 40 now travels through an additional distance to bring the tip 70 into the dispensing position relative to the cartridge 22. The value of the additional distance of positional travel is based on data stored in the memory 154. The microprocessor 62 reads the memory 154 to obtain the travel data. A person calibrating the test system 20, in accordance with the invention, provides the requisite data on additional travel based on a knowledge of a reference point which, in a preferred embodiment, is the height of the cartridge 22 relative to a top surface 158 of the carousel 24. This height data is entered via an entry device 156 to the memory 154. By way of example, the entry device 156 may be constructed as a touch panel located at a position of convenience to an operator of the system 20

Figure 6:
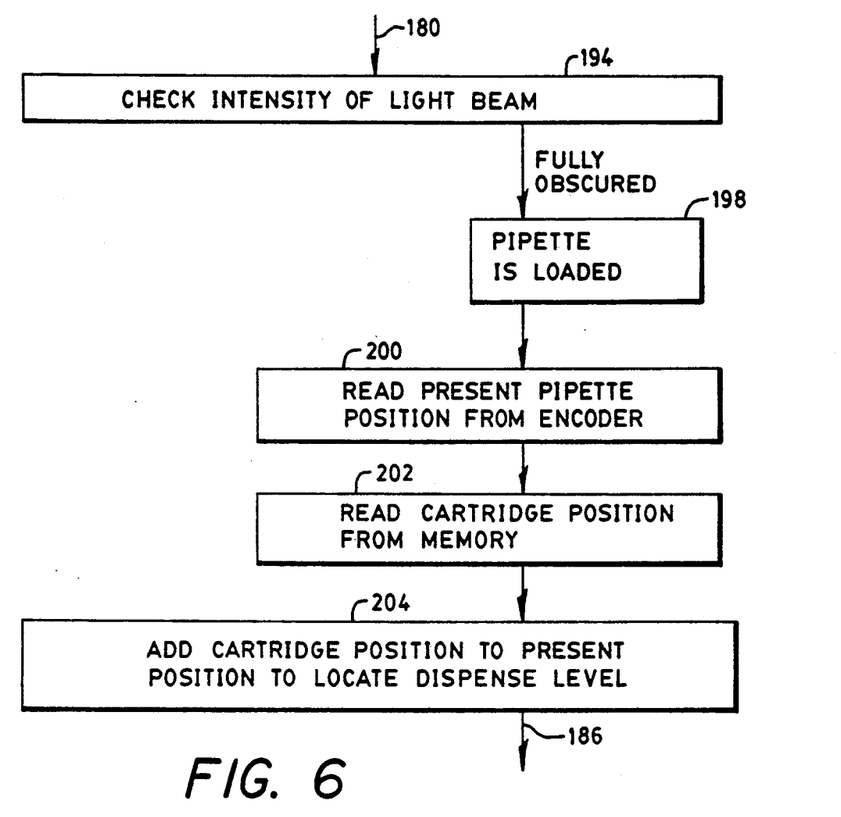
FIG. 6 shows details in a block of the chart of FIG. 5 relating to the computation of additional pipette travel.
Figure 7:
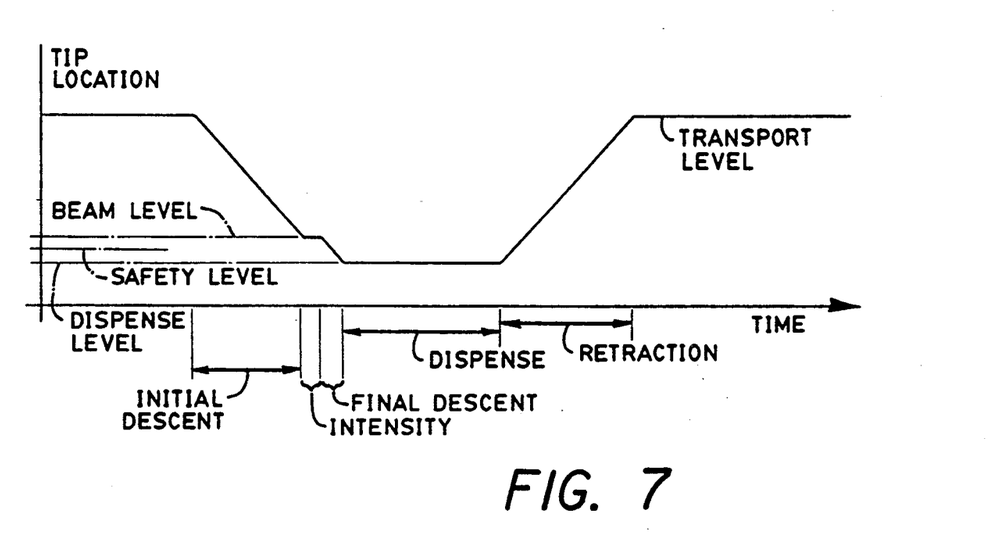
FIG. 7 is a timing diagram showing vertical movement of the pipette.

The operation of the feedback circuit 142 may be explained further with reference to FIG. 2 and with reference to the timing diagram of FIG. 7. Prior to the lowering of the pipette 40, the tip 70 is at a sufficiently high elevation to permit transporting the pipette 40 in the X direction between the carousel 24 and the table 68. This is referred to in FIG. 7 as the transport level. The pipette 40 then undergoes its initial descent during an interval of time identified in FIG. 7. The initial descent interval ends with the breaking of the light beam 114. Thereupon, there is the final interval of descent in which the pipette 40 descends the additional travel. This brings the pipette tip to the dispense level indicated in FIG. 7. After completion of a dispensing interval of time, the feedback circuit 142 raises the pipette 40 back to the transport level during a retraction interval shown in FIG. 7. Also shown in FIG. 7 is a safety level which will be described with reference to the flow charts of FIGS. 5–6.

Figure 5:
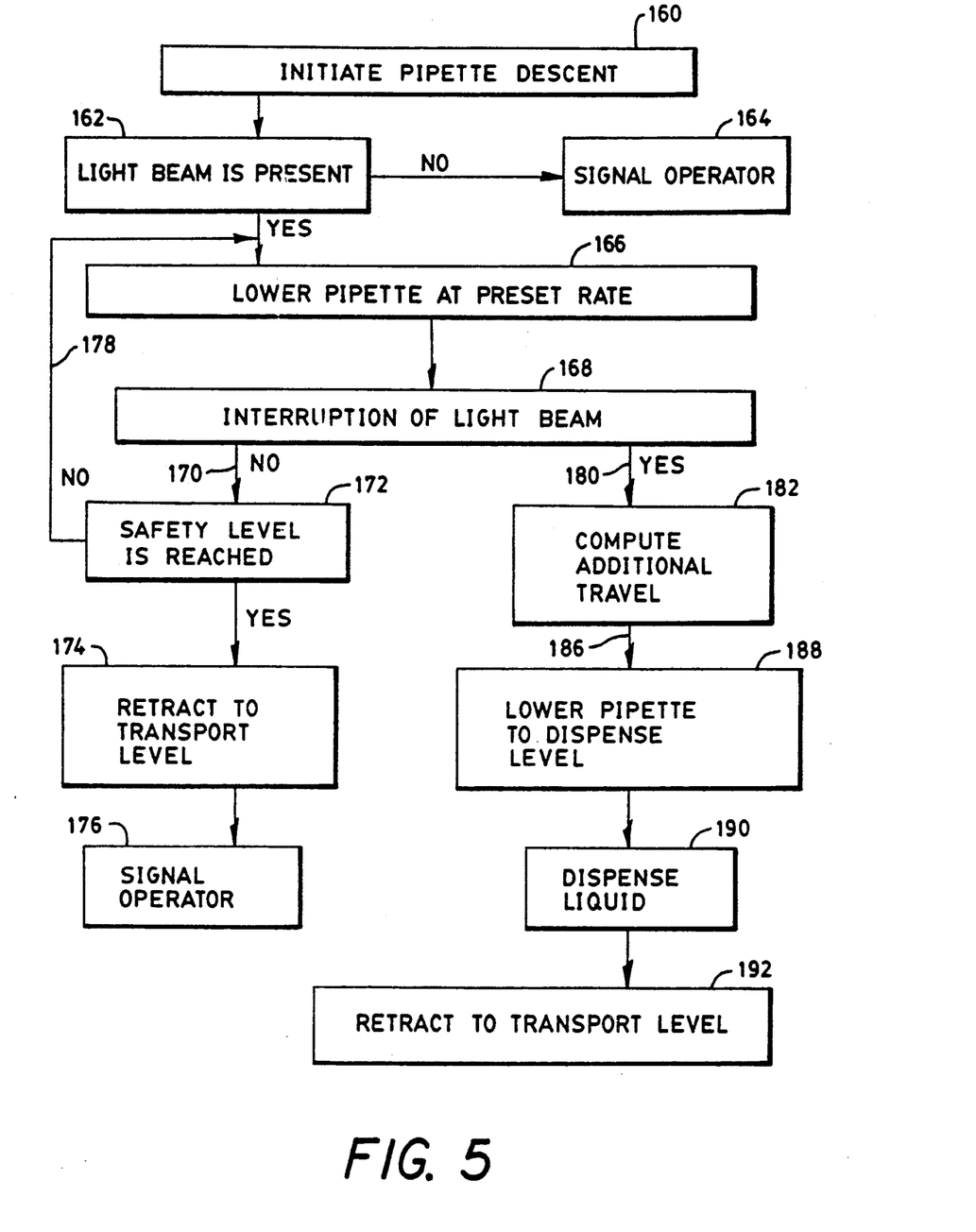
FIG. 5 is a flow chart showing operation of the microprocessor.

With reference to FIG. 5, the inventive feature of lowering the pipette to the cartridge 22 while compensating for variations in positions of the tip 70 is explained with reference to a flow chart. The flow chart describes operation of the microprocessor 62 of FIG. 2 for operating the vertical pipette drive 78 (FIGS. 2 and 4) for lowering the pipette 40 to dispense liquid reagent in a compartment 106 of the cartridge 22. Initiation of the pipette descent toward the cartridge 22 occurs at block 160. At block 162, the determination is made as to whether the light beam 114 (FIG., 2) is present. The microprocessor 62 is informed as to the status of the light beam by the signal outputted by the comparison circuitry 118. When the pipette 40 is in an elevated position, there is no blockage of the light beam 114 and, accordingly, the light beam 114 should be present and the comparator 120 should be outputting the logic-1 signal indicating full intensity of the light beam 114. If the beam is not present, then, at block 164, a person operating the test system 20 is signaled to correct an apparent fault in the equipment of the system 20.

If the light beam is present, the procedure advances to block 166 wherein the microprocessor 62 directs the lowering of the pipette 40 in the manner described above with reference to FIG. 4. Therein, the microprocessor 62 continually inputs new positions along the path of travel of the pipette 40 at a rate commensurate with the dynamic response of the feedback loop 142. Periodically, during the lowering of the pipette 40, the microprocessor 62 observes output signals of the comparison circuitry 118 to determine whether there has been an interruption of the light beam 114, this determination being performed at block 168.

Assuming that no interruption of the light beam 114 by the pipette 40 has occurred, then operation proceeds along line 170 to block 172 to determine whether the safety level (shown in FIG. 7), has been reached. There is the possibility of a system malfunction wherein the stem 72 of the pipette 40 has failed to secure the tip 70 at the table 68. This could occur for a variety of reasons, such as operator negligence in filling the table 68 with the set of tips 70, or the possibility of a cracked tip which fails to provide adequate friction for securing the tip to the stem 72. Since the shaft angle encoder 152 (FIG. 4) continually outputs position data to the microprocessor 62, the microprocessor 62 has knowledge of the location of the distal end of the stem 72. As the distal end of the stem 72 approaches the vicinity of the light beam 114, there should be an interruption of the beam 114 by the tip 70, assuming the tip 70 is present. The safety level is the lowest point at which the microprocessor 62 will allow the stem 72 to drop without interruption of the beam 114. If the safety level is reached, then the microprocessor 62 concludes that the tip 70 is absent, and operation proceeds to block 174 wherein the microprocessor 62 orders retraction of the pipette 40 to the transport level. As noted hereinabove, at the transport level, the pipette 40 clears the top wall 104 of the incubator 36 so that the stem 72 is fully visible to an operator for performing remedial action. From block 174, operation proceeds to block 176 wherein the operator is signaled to take remedial action.

During normal operation of the system 20, the tip 70 is present on the stem 72 and, accordingly, at block 172 the safety level would not be reached without interruption of the light beam 114. Accordingly, operation proceeds from block 172 along line 178 back to block 166 wherein the microprocessor 62 continues to lower the pipette at the preset rate. The operation continues in repetitive fashion through the blocks 166, 168, and 170 until interruption of the light beam 114 occurs at line 180. The interruption of the light beam 114 is signaled to the microprocessor 62 by a change in the output signal of the comparison circuitry 118 such that the signal changes from logic-1 to logic-0.

Assuming that the tip 70 is present, then, upon the interruption of the light beam at line 180, the output signal of the comparison circuitry 118 is at logic-0 to indicate to the microprocessor 62 that the tip 70 is filled with the liquid reagent, and that the tip 70 has reached the position of the light beam 114 along the path of travel of the tip 70 towards the cartridge 22. Accordingly, at block 182, the microprocessor 62 determines the position of the dispense level (FIG. 7) so as to compute the additional amount of travel required by the tip 70 to reach the dispense level. The operation within block 182 will be described in further detail with reference to FIG. 6.

In FIG. 5, the operation proceeds from block 182 via line 186 to block 188 wherein the pipette 40 is lowered further to locate the tip 70 at the dispense level. This lowering of the pipette is accomplished, in the manner disclosed hereinabove with reference to the feedback circuit 142 of FIG. 4, wherein the microprocessor 62 inputs further locations along the travel path of the pipette to bring the tip 70 to the dispense level. Thereafter, at block 190 the microprocessor 62 commands the suction control unit 128 to dispense liquid to the selected compartment 106 of the cartridge 22. Thereafter at block 192, the pipette 40 is retracted back from the cartridge 22 to the transport level. The system 20 can now initiate other steps in the testing procedures carried out by various ones of the cartridges 22.

FIG. 6 shows details in the procedure of block 182 (FIG. 5) for checking the filling of the pipette tip followed by the computation of the additional travel of the pipette. The procedure at line 180 proceeds to block 194 to check the intensity of the light beam. In the event that, at block 194, the light is fully obscured, the signal of the comparison circuit 118 is at logic-0, as was noted hereinabove, which allows the microprocessor 62 to determine, at block 198, that a loaded pipette is present. Thereupon, at block 200 the microprocessor reads the present pipette position as outputted by the encoder 152 (FIG. 4). This is followed, at block 202, by a reading of the position data of the cartridge 22, which data has been stored in the memory 154 (FIG. 4).

The cartridge position data designates the location of a top surface of the cartridge 22 relative to the top surface 158 of the carousel 24. Since the distance between the light beam 114 and the carousel surface 158 is known and fixed, the inputting of this cartridge data is equivalent to giving the microprocessor the distance between the top surface of the cartridge 22 and the beam 114. Accordingly, at block 204, the additional distance between the beam 114 and the cartridge 22 is added to the vertical distance already traveled by the pipette 40, the vertical distance being provided by the encoder 152. This gives the reading of the encoder 152 which will be obtained when the pipette tip 70 reaches the dispense level. This information is used by the microprocessor 62 in operating the circuit of FIG. 4 for continued lowering of the pipette 40. Accordingly, the operation can now proceed via line 186 to block 188 as has been disclosed above with reference to FIG. 5.

The timing diagram of FIG. 7 has already been referred to in the description of the circuitry of FIG. 4 and the procedure of FIGS. 5 and 6. Briefly, the diagram of FIG. 7 shows the descent of the pipette tip 70 at a fixed rate during the initial descent interval. This is followed by a pause in which the condition of the light beam is observed, followed by the final descent in which the pipette tip 70 is brought to the dispense level. At the conclusion of the dispense interval, the tip 70 is retracted to the transport level. The safety level is disposed between the light beam level and the dispense level.

The foregoing description provides for operation of the test system 20 in a fashion which allows the pipette to be lowered with an accuracy which is independent of the position of the pipette tip 70 on the pipette stem 72.

Figure 8:
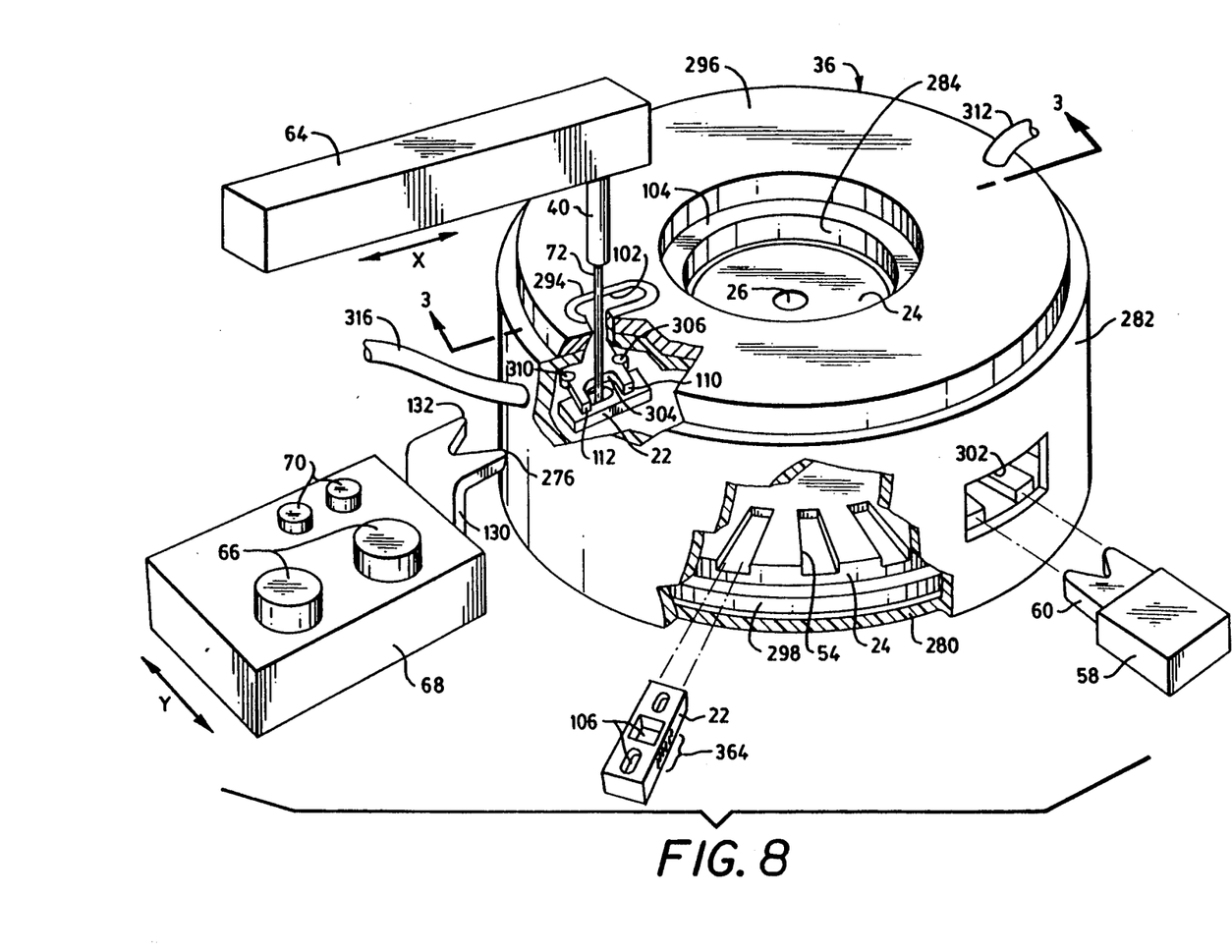
FIG. 8 is a further view of the test system of FIG. 1 with portions of the system indicated diagrammatically, FIG. 8 including a perspective view of an incubator with portions shown cut away to disclose interior components of the incubator.

With reference to FIGS. 1 and 8, there is provided further details in the construction of a preferred embodiment of the incubator 36 and its operation with the system 20. In addition to the top wall which serves as the roof 104 of the incubator 36 and is located above the carousel 24, the incubator 36 further comprises a bottom wall which serves as a floor 280 of the incubator 36 and is located below the carousel 24, and two sidewalls wherein one of the sidewalls is an outer wall 282 which extends from the roof 104 to the floor 280 and the second of the sidewalls is an inner wall 284 which extends from the roof 104 toward a central portion of the carousel 24. The roof 104 has an annular shape. An upper region 286 of the incubator 36 is bounded by the roof 104, the top surface 158 of the carousel 24, the outer wall 282 and the inner wall 284. The upper region 286 of the incubator 36 has a toroidal shape. The slot 102 in the roof 104 is relatively narrow, and is surrounded by a grommet 294. The slot 102 has a width large enough to clear the stem 72 and the tip 70 mounted on the distal end of the stem 72.

The incubator 36 further comprises two heaters, namely, a top heater 296 supported by the roof 104, and a bottom heater 298 supported by the floor 280 for controlling the incubator temperature. The bottom heater 298 is located in a lower region 300 of the incubator 36, between the carousel 24 and the floor 280. An injection port 302 is provided in the outer wall 282 facing the injector 58 to provide access to the arm 60 for inserting a cartridge 22 in a berth 54 of the carousel 24, and for extracting the cartridge 22 from the berth 54. A frame 304 is located within the upper region 286 for supporting sensors useful in the operation of the system 20, one such sensor 306 being provided for sensing the incubator temperature. The frame 304 is secured by a bracket 308 to the outer wall 282. By way of example in the construction of the frame 304, the frame 304 may be constructed as a circuit board for supporting electronic circuitry (not shown) such as a preamplifier for amplifying electrical signals provided by the sensor 306. By way of further example, an additional sensor 310 may also be mounted on the frame 304 for sensing the humidity because there are tests in which the humidity affects the outcome of the test, and a knowledge of the humidity can provide a more accurate reading of the test. Electrical cables 312, 314, and 316 connect respectively with the top heater 296, the bottom heater 298, and the sensors 306 and 310 for connecting these components to circuitry outside of the incubator.

In accordance with the invention, accurate calibration of the system 20 is accomplished by a procedure which begins by removing the pipette tip 70 from the stem 72, and replacing the tip 70 with an indicator 320 (FIG. 9), and by providing a set of targets 322, 324, 326, and 328 shown in FIG. 2. The targets 322 and 324 are located on opposite ends of the tray 67. The targets 326 and 328 are located on opposite ends of the tray 69. A further target 330 (FIG. 13) is located on a dummy cartridge 332 which is to be inserted into the berth 54 (FIG. 2) of the carousel 24 in place of the cartridge 22 during the calibration procedure. The indicator 320 is machined precisely to establish a specific spacing between a distal end 334 of a pointer 336 at the bottom end of the indicator 320 (FIGS. 9 and 10) and a distal end 338 (FIG. 11) of the stem 72. As will be described in further detail, hereinafter, the pointer 336 is placed sequentially on all of the targets 322-330 so as to precisely locate the distal end 338 of the stem 72 relative to the trays 67 and 69 and to the dummy cartridge 332. In the case of the dummy cartridge 332, the target 330 is located at an arbitrarily chosen point selected in this illustrative instance to be approximately mid-way between the dispense and/or aspiration positions in the X direction for the assay cartridge(s). As shown, the target 330 is positioned in the plane of the top surface 331 of cartridge 332.

The calibration procedure is predicated on the presence of reference positions for all of the drives of the system 20, namely, the reference position for the carousel 24 driven by the motor 28, a reference position for the base 88 driven by the X-drive motor 90, a reference position for the table 68 driven by the Y-drive motor 100, and a reference position of the pipette 40 driven in the Z direction by the drive motor 86. The detection system 108 (FIG. 2) disposed above the carousel 24 provides a reference position for movement of the pipette 40 in the Z direction in the situation wherein the pipette tip 70 has entered the interior of the incubator 36 via the slot 102. However, in the situation wherein the pipette 40 is located above the table 68, a further optical position detector 340 is required. The detector 340 is a well-known commercially-available optical position detector, operating in the manner of the detection system 108, and includes a source and a sensor of radiation (not shown) mounted on the base 88 with a flag (not shown) extending outwardly from the pipette 40 to break the beam of light upon passage of the flag between the light source and the light sensor of the detector 340. The breaking of the beam of light provides an indication of the position of the flag and, hence, the position of the pipette 40 relative to the base 88. For optimum accuracy in the measurement of the position, the light beam should be broken upon motion of the pipette 40 in a predetermined direction, such as downward motion. Another position detector 342 is disposed on an interior wall of the beam 74 and acts with a flag carried by the base 88 for establishing a reference position in the X direction of motion. A further position detector 344 is disposed on the rail 76 and acts with a flag carried by the table 68 for measuring a reference position of the table 68 during movement in the Y direction. Also, a position detector 346 is disposed on a wall of the incubator 36 and acts with a flag carried by the carousel 24 for establishing a reference angular orientation or position of the carousel 24. The detectors 342-346 are constructed in the same fashion as the detector 340.

With reference to FIGS. 9-12, the indicator 320 is configured in the shape of a barrel having an outer circular wall 348 and a base 350 connecting with the wall 348 for closing off a bottom end of a central cavity 352 formed by the wall 348. The pointer 336 extends downwardly from the base 350. An upper region of the cavity 352 has a circular cylindrical shape, and a lower portion of the cavity 352 has a frusto-conical shape for receiving a tapered end portion 354 of the stem 72.

Figure 11:
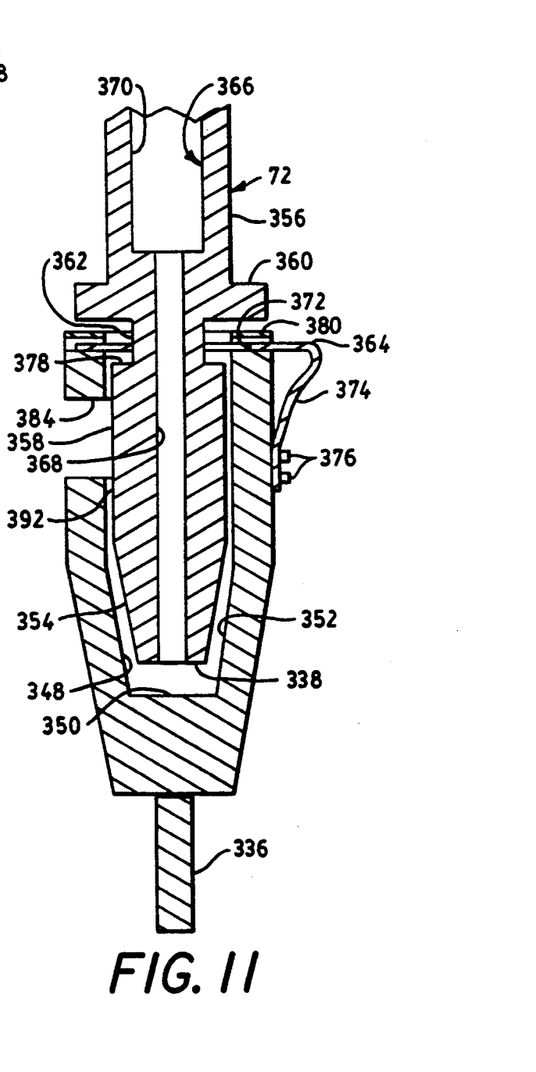
FIG. 11 is a longitudinal sectional view of the stem and indicator taken along the line 11—11 in FIG. 10.
Figures 12, 13:
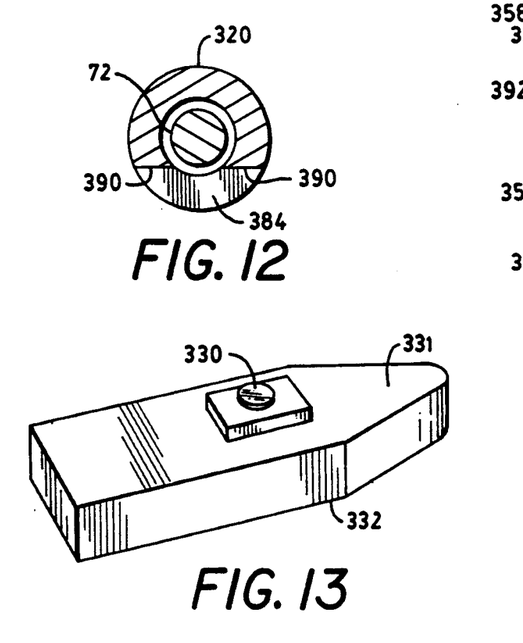
FIG. 12 is a transverse sectional view of the stem and indicator taken along the line 12—12 in FIG. 10.
FIG. 13 is a perspective view of a dummy cartridge having a target thereon.

The stem 72 has a circular cylindrical housing 356, a portion 358 of the housing 356 extending into the cavity 352 upon insertion of the stem 72 into the indicator 320. The housing portion 358 terminates in the tapered end portion 354 at a lower end of the stem 72, and extends upward to a flange 360 which encircles the stem 72, and extends radially outward of the stem 72. The upper end of the housing portion 358, immediately below the flange 360 necks down by a circumferential slot 362, the slot 362 receiving a spring-loaded tab 364. Also included in the stem 72 is an elongated central passage 366 for the conduction of liquid, the passage 366 being formed of a relatively narrow bore 368 at the housing portion 358, and a relatively wide bore 370 communicating with the narrow bore 368 and being located at an upper end of the stem 72.

In operation, the housing portion 358 of the stem 72 is inserted into the cavity 352 of the indicator 320 by passing the tapered end portion 354 through an aperture 372 in the tab 364. The tab 364 curves in the form of a handle 374 which is secured by screws 376 to the outer wall 348 of the indicator 320. Spring force developed within the tab 364 urges the tab to the right, with reference to the view of FIG. 11, so that a left edge of the aperture 372 is urged into the slot 362 so as to trap the stem 72 within the indicator 320. The width of the slot 362 is much greater than the thickness of the tab 364 so that the stem 72 can slide along the axis of the indicator 320, the sliding being limited by abutment of the tab 364 against a lower wall 378 of the slot 362. Sliding is limited in the reverse direction by abutment of a top edge 380 of the indicator 320 against the bottom of the flange 360 of the stem 72. The displacement of the tab 364 in a direction transverse to the longitudinal axis of the indicator 320 is provided within a guide 382 formed within the top portion of the indicator 320.

A window 384 is provided in the wall 348 of the indicator 320 for viewing the housing portion 358 of the stem 72. Alignment marks 386 are provided on the stem 72 at a location centered within the window 384 upon insertion of the stem 72 into the indicator 320. A second set of alignment marks 388 are disposed on the indicator 320 located on side panels 390 of the window 384. The marks 386 are formed as two parallel bands disposed circumferentially about the stem 72. The marks 388 are formed as two parallel bands lying in planes transverse to the longitudinal axis of the indicator 320. In a preferred embodiment of the invention, spacing between the bands, as measured on centers of the marks 386 is equal to that of the marks 388. The inner diameter of the indicator wall 348 is sufficiently large to provide for a clearance gap 392 between indicator 320 and stem 72 to facilitate sliding of the stem 72 within the indicator 320.

Figures 9, 10:
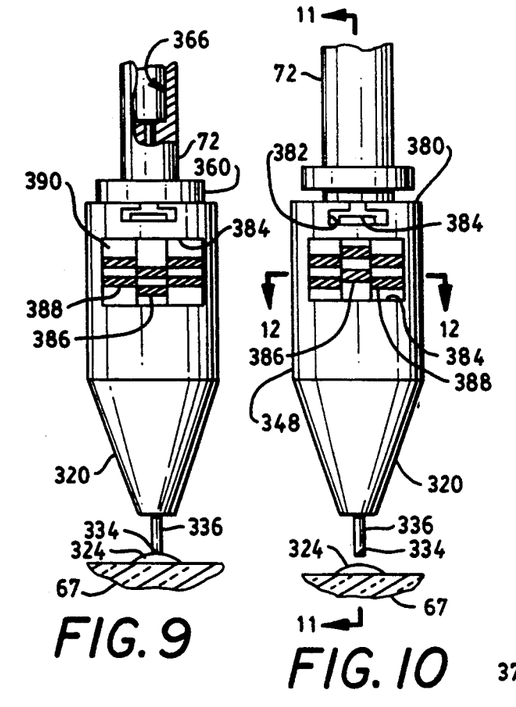
FIG. 9 is a side elevation view, partially sectioned, showing a pipette holder stem inserted into an indicator, the indicator being in contact with a target.
FIG. 10 shows a side elevation view of the pipette holder stem inserted into the indicator of FIG. 9 with the indicator being held above and spaced apart from the target.

FIG. 9 shows the situation, by way of example, in which the pipette 40 is being lowered upon the target 324 of the tray 76. FIG. 9 demonstrates the situation in which the stem 72 has been lowered the maximum amount at which point the flange 360 abuts the top edge of the indicator 320. In this situation, as portrayed in FIG. 9, the marks 386 appear to be lower than the marks 388. In FIG. 10, the stem 72 is being raised sufficiently such that the indicator 320 clears the target 324. In this situation, the stem 72 has been slid upwardly through the indicator 320 the maximum amount, the sliding being limited by abutment of the tab 364 against the lower wall 378 of the slot 362 in the stem 72. In the situation of FIG. 10, the marks 386 of the stem 72 appear to be higher than the marks 388 of the indicator 320.

During the alignment procedure, an operator of the system 20 directs the stepping motors to move the stem 72 with incremental motion, such as one step of the motor at a time, so as to center the pointer 336 upon a target, such as the target 324, and to bring the set of marks 386 into alignment with the set of marks 388. The indicator 320 has been previously calibrated to state the distance between the distal end 338 of the stem 72 and the distal end 334 of the pointer 336 in the condition of alignment of the set of marks 386 with the set of marks 388. By way of example, incremental control of the stepping motor, such as the motor 86 (FIG. 4) may be accomplished by use of the stepping motor controller 150 responsive to command signals entered via the data entry device 156. Output pulses for driving the motor 86 may be applied by the controller 150 to the motor 86. Similar incremental operation of the other motors 28, 100 and 90 (FIG. 2) may be implemented similarly by other step controllers (not shown) such as the controller 150.

In the operation of the system 20, the location coordinates of each of the targets 322-330 relative to the reference positions of the detectors 340-346 are stored in the memory 154. This enables the microprocessor 62 to locate the pipette 40 at any one of the targets upon direction of an operator entering appropriate commands to the data entry device 156. However, it is recognized, that during manufacture of the system 20, there may be a small displacement of the pipette from a desired location at a target or from any one of the reservoirs 66 on the tray 76 or from the pipette tips 70 in the tray 69 or from the compartment 106 of the cartridge 22 beneath the slot 102. Such small displacements from optimum position may introduce errors in the assay process. These minor displacements are corrected by the calibration procedure of the invention so that optimum tests results are obtained during operation of the system 20.

Figure 14:
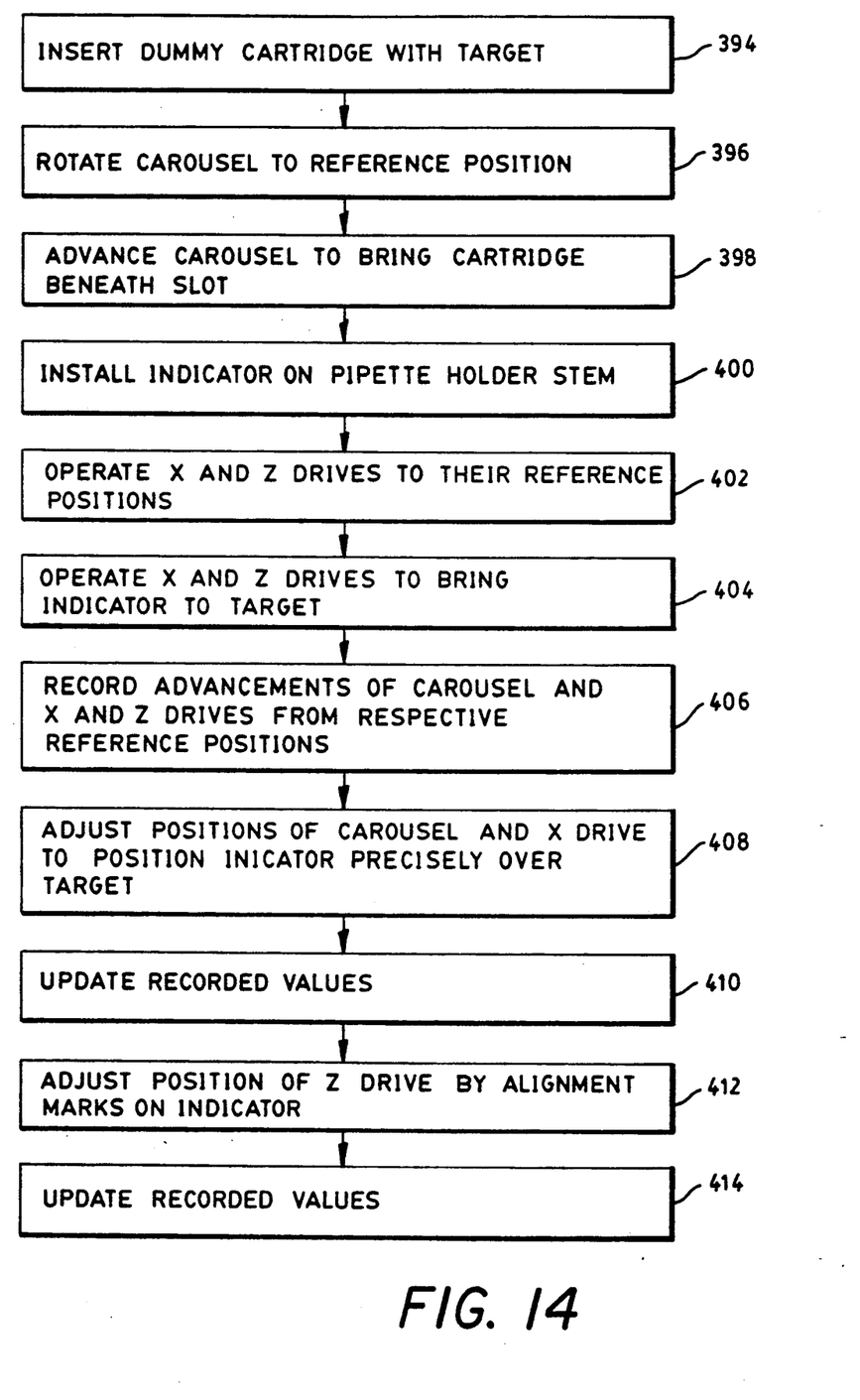
FIGS. 14 and 15 are flow charts setting forth procedural steps of position calibration, including operation of a microprocessor of the system.
Figure 15:
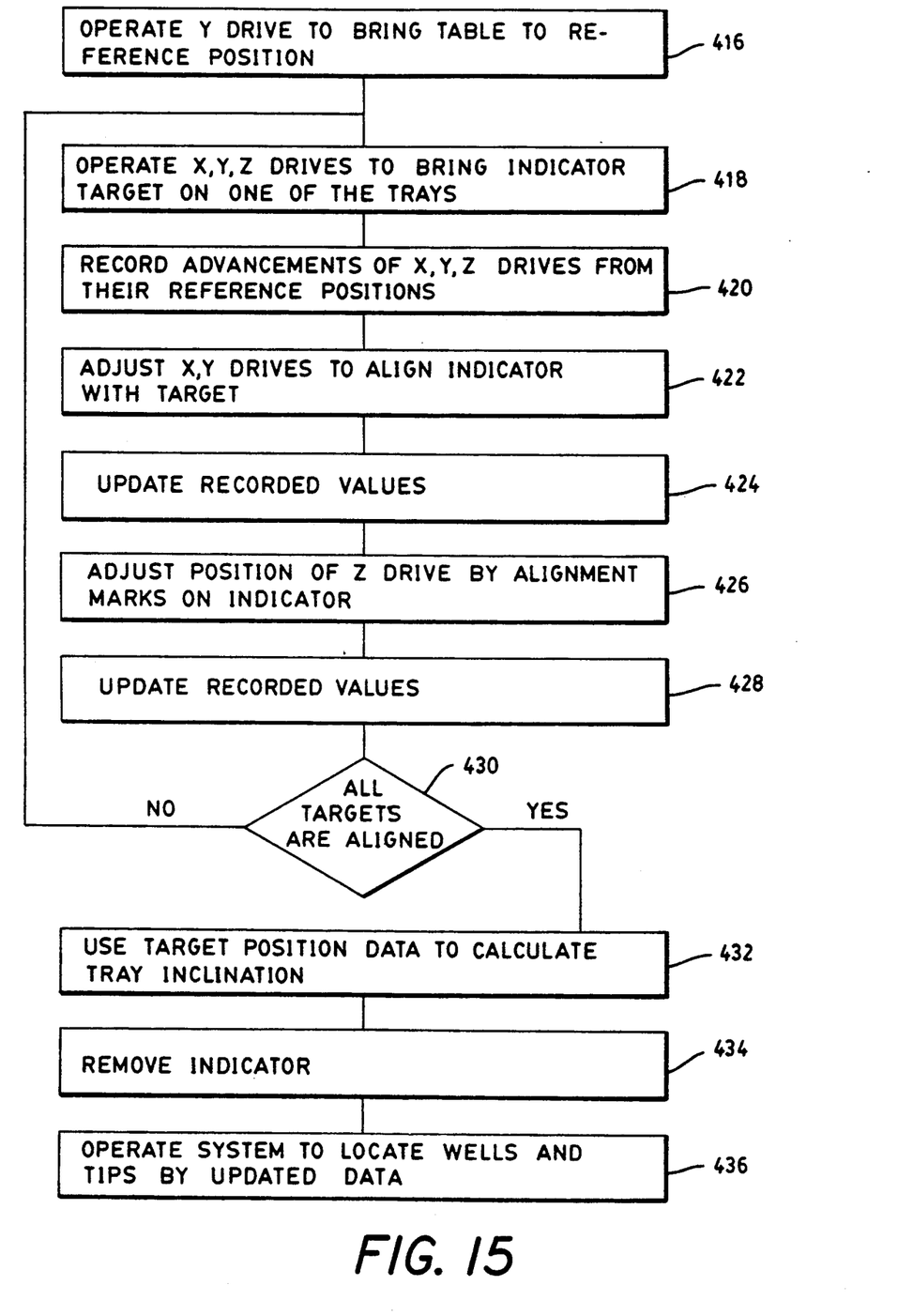

FIGS. 14 and 15 show flow charts describing the calibration procedure. In FIG. 14, the procedure begins at block 394 by insertion of the dummy cartridge with the target into a berth of the carousel. Thereupon, the carousel is rotated to the reference position, at block 396, and is further rotated at block 398, to bring the cartridge beneath the slot in the roof the incubator. The number of steps applied to the stepping-motor drive of the carousel is counted by the microprocessor so that the present position of the carousel, relative to the reference position, is known by the microprocessor. The indicator is to be installed on the pipette holder stem; this may be done at the beginning of the procedure or, alternatively, must be done at least by block 400. Thereupon, at block 402, the X drive and the Z drive are operated to bring the pipette stem and indicator to the reference positions of the X drive and the Z drive. The X and the Z drives are operated further, at block 404 to bring the indicator to the target on the dummy cartridge.

At block 406, the advancements of the carousel drive, the X drive and the Z drive from their respective reference positions are recorded in the microprocessor memory. Thereupon, at block 408, the positions of the carousel and of the X drive are adjusted incrementally by pulsing the stepping motors of these drives, possibly at one pulse at a time, to position the indicator precisely over the target. The updated positions of the carousel drive and the X drive relative to the reference positions are recorded in the microprocessor memory at block 410. Then, at block 412, the position of the Z drive is adjusted incrementally by pulsing the stepping motor, possibly one pulse at a time, to bring the alignment marks of the indicator in registration with the alignment marks on the pipette holder stem. This places the distal end of the stem at a known height above the target, the height being inscribed on the indicator based on a previous calibration of the indicator. At block 414, the operator reads the value of height, inscribed on the indicator, and enters this value into the microprocessor memory by means of a suitable data entry device such as a keyboard or touch panel having soft keys. This completes the alignment process for the target of a cartridge on the carousel. It should be noted here that the present calibration technique permits alignment of the target position on the cartridge within the incubator while the alignment marks on the pipette stem and the indicator device, respectively, are above the incubator and therefore easily visible to the operator.

In FIG. 15, the calibration procedure continues for calibration of target positions on the trays carried by the table. It is recognized that there are numerous cups or reservoirs and pipettes within the trays. The microprocessor is provided with stored data as to the locations of the reservoirs and the pipettes in their respective trays. However, there is a possibility that the tray may be offset from its presumed position, or that there may be a tilt in the tray. Calibration of the target positions at the opposite ends of the tray enable the microprocessor to compensate for any position errors of the tray by adding a tray offset value to the previously stored values of the positions of the reservoirs and the pipettes. Also, in the event that there is an inclination of a tray from its presumed attitude, whether this inclination be in the horizontal or vertical plane, knowledge of the target locations at the ends of the trays enable the microprocessor to interpolate the positions of the reservoirs and the pipettes to compensate for such misalignment of one or more of the trays. Such interpolation procedures are well known and need not be described in detail herein.

The Y drive is operated to bring the table to its reference position, this being performed at block 416. Thereupon, the Y drive of the table and the X and the Z drives of the transport are operated, at block 418, to bring the indicator to a designated target on one of the trays. Thereupon, at block 120, the advancement position of the Y drive of the table and the X and the Z drives of the transport from their respective reference positions are recorded.

At block 422, the X and the Y drives are adjusted to align the indicator in a horizontal plane with the target. It is noted that incremental movement of the Z drive for vertically positioning the indicator can be accomplished in steps of any desired magnitude. In a preferred embodiment the incremental movement in the Z drive is about 3 mils (0.076 mm) while, in the horizontal directions of the X and the Y drives, the minimum incremental advancement is a step having a size of 10 mils (0.254 mm). The updated values of the positions of the X and the Y drives are recorded in the microprocessor memory at block 424. Thereupon, at block 426, the vertical position of the indicator relative to the designated target is adjusted by operation of the Z drive. The Z drive is operated incrementally by pulsing the stepping motor, possibly at a rate of one pulse at a time, to bring the alignment marks of the indicator in registration with the alignment marks of the stem. Thereupon, at block 428, the updated value of the vertical position of the distal end of the stem relative to the designated target is entered manually into the microprocessor memory by the operator, the value being inscribed on the indicator.

The foregoing procedure, beginning at block 418 provides data as to the target at one end of a tray. For the situation of a table carrying two trays, there are a total of four targets on the trays. At block 430, the question is raised as to whether all of the four targets have been calibrated. In the event that the answer is no, operation reverts to block 418 to provide calibration data for the target at the opposite end of the tray. The procedure continues via block 430 until all of the targets have been calibrated, Thereupon, operation proceeds to block 432 wherein the microprocessor uses the target position data to calculate tray inclination, this being followed by use of the inclination data to offset the basic position data of reservoirs and pipettes which was installed in the microprocessor memory at the time of manufacture of the system. The calibration procedure has now been completed, and the indicator is removed at block 434 followed by operation of the system in its normal mode of operation. However, in the normal mode of operation, as noted at block 436, the positioning of the pipette at the various wells and other locations is based on updated data of the locations of the dummy cartridge and of the trays carried by the table.

Thereby, the invention has increased the accuracy in the performance of assays by the automated test system.

It is to be understood that the above described embodiment of the invention is illustrative only, and that modifications thereof may occur to those skilled in the art. Accordingly, this invention is not to be regarded as limited to the embodiment disclosed herein, but is to be limited only as defined by the appended claims.

What is claimed is:

1. A method of calibrating the pipette position in an automated assay instrument employing a conveyor for carrying assay cartridges and a transport for transporting a pipette between different locations, the position of the pipette and the conveyor being controlled automatically by a microprocessor, the method comprising steps of:

slidably attaching an indicator device on a pipette holder stem of a pipette assembly, each of said indicator device and said pipette holder stem carrying alignment indicia sequencing positions of the pipette to locate a target said sequencing step including the steps of translating said stem by a pipette assembly transport means to a location above a target, lowering said stem until contact is made between said indicator device and said target, lowering said stem an additional distance with sliding between said indicator device and said stem to align the indicia of said indicator device and said stem, and entering a reference height of said indicator, indicative of the distance between said stem and said target, into a microprocessor; and removing said indicator device from said stem.

2. The method according to claim 1 wherein said instrument includes a tray carrying a plurality of reservoirs for holding fluid and a first target at a first location and a second target at a second location, and wherein said sequencing step is carried out for said first target and for said second target, and wherein said microprocessor utilizes data from both targets to determine the attitude of the tray.

3. The method according to claim 1 wherein said target is located on a cartridge carried by said conveyor.

4. The method as defined in claim 3 wherein said conveyor is a carousel and further comprising a step of rotating the carousel to bring the cartridge into alignment with a path of travel of the pipette stem, said transport means moving the pipette stem along a path of travel intersecting the rotational axis of the carousel.

5. The method according to claim 4 wherein said instrument includes a tray carrying a plurality of reservoirs for holding fluid and a first target at a first location and a second target at a second location, and
wherein said sequencing step is carried out sequentially for said target on said cartridge and for each of said first and second targets on said tray.

6. The method according to claim 5 wherein said carousel is rotatable in both clockwise and counterclockwise directions about its axis of rotation, the pipette stem is movable along a path parallel to a radius of the carousel and along a path parallel to the rotational axis of the carousel, and wherein said instrument further includes a first detector of a reference position of the carousel, a second detector of a reference position of the pipette stem along a path parallel to the carousel radius and a third detector of a reference position of the pipette stem along a path parallel to the rotational axis of the carousel,
the method including the further steps of rotating the carousel to its reference position prior to performance of said sequencing step, adjusting the position of the carousel by incremental rotation of the carousel to bring the target on said cartridge into alignment with the indicator and entering into the microprocessor the rotational position of the carousel.

7. A method according to claim 5 wherein the carousel is rotatable in both clockwise and counterclockwise directions about its axis of rotation, the pipette stem is movable along a path parallel to a radius of the carousel and along a path parallel to the rotational axis of the carousel, said instrument including a first detector of a reference position of the carousel, second detector of a reference position of the stem along a path parallel to the carousel radius and a third detector of a reference position of the stem along the path parallel to the rotational axis of the carousel;
the method further comprising the steps of moving the stem along the path of travel parallel to the carousel radius to the reference position of the second detector, adjusting the position of the stem along the path parallel to the carousel radius by incremental movement to bring the indicator into alignment with the first target on the tray; and
entering into the microprocessor the location of the stem along the path parallel to the carousel radius.

8. A method according to claim 7 wherein the tray is carried by a movable table for positioning the tray along a third path perpendicular to both of the foregoing paths; and
wherein the method comprises a further step of adjusting the tray by incremental movement along said third path to bring the first target on the tray into alignment with the indicator.

9. A method according to claim 5 wherein the carousel is rotatable in both clockwise and counterclockwise directions about its axis of rotation, the pipette stem is movable along a path parallel to a radius of the carousel and along a path parallel to the rotational axis of the carousel, said instrument including a first detector of a reference position of the carousel, a second detector of a reference position of the stem along a path parallel to the carousel radius and a third detector of a reference position of the stem along the path parallel to the rotational axis of the carousel;
the method further comprising the steps of moving the stem along the path of travel parallel to the carousel axis to the reference position of the third detector, and adjusting the position of the stem along the path parallel to the carousel axis by incremental movement to bring the indicator into alignment with the first target on the tray; and
entering into the microprocessor the location of the stem along the path parallel to the carousel axis.

10. A method according to claim 1 wherein said step of removing the indicator includes a step of raising the pipette stem to clear the indicator from the target.

11. A method according to claim 1 wherein said pipette stem includes a circumferential slot around the stem, said indicator includes a spring-loaded tab for engagement within the circumferential slot upon insertion of the stem into the indicator, the slot extending along the stem axis to define a slot width which is greater than the corresponding dimension of the tab so as to permit limited sliding motion of the tab within the slot; and
wherein the method further comprises the steps of limiting a sliding movement of the indicator along the stem by means of said tab and said slot, and locking the indicator to the stem by emplacement of said tab in said slot.

* * * * *